US009304090B2

(12) United States Patent
Cordingley

(10) Patent No.: US 9,304,090 B2
(45) Date of Patent: Apr. 5, 2016

(54) SYSTEMS AND METHODS FOR PROVIDING POLARIZATION COMPENSATED MULTI-SPECTRAL LASER REPAIR OF LIQUID CRYSTAL DISPLAY PANELS

(71) Applicant: GSI Group Corporation, Bedford, MA (US)

(72) Inventor: James J. Cordingley, Littleton, MA (US)

(73) Assignee: Electro Scientific Industries, Inc., Portland, OR (US)

( * ) Notice: Subject to any disclaimer, the term of this patent is extended or adjusted under 35 U.S.C. 154(b) by 542 days.

(21) Appl. No.: 13/793,190

(22) Filed: Mar. 11, 2013

(65) Prior Publication Data

US 2014/0256205 A1 Sep. 11, 2014

(51) Int. Cl.
G02F 1/13 (2006.01)
G01N 21/95 (2006.01)
G02F 1/1335 (2006.01)

(52) U.S. Cl.
CPC .............. *G01N 21/95* (2013.01); *G02F 1/1309* (2013.01); *G02F 1/133514* (2013.01); *G02F 2201/508* (2013.01)

(58) Field of Classification Search
CPC .............................. G01N 21/95; G02F 1/1309
USPC ............................ 219/121.68, 121.83, 121.74
See application file for complete search history.

(56) References Cited

U.S. PATENT DOCUMENTS

| 5,017,755 | A | * | 5/1991 | Yahagi | G02F 1/13439 |
| | | | | | 219/121.68 |
| 5,142,386 | A | | 8/1992 | Ishihara | |
| 5,212,374 | A | * | 5/1993 | Speedy | G01R 31/308 |
| | | | | | 250/201.1 |
| 6,501,061 | B1 | | 12/2002 | Kitai et al. | |
| 6,812,992 | B2 | | 11/2004 | Nemeth | |
| 7,502,094 | B2 | | 3/2009 | Son | |
| 7,636,148 | B2 | | 12/2009 | Yoo et al. | |
| 7,697,108 | B2 | | 4/2010 | Nam et al. | |
| 7,755,380 | B2 | | 7/2010 | Park et al. | |

(Continued)

FOREIGN PATENT DOCUMENTS

| JP | 2007241274 A | 9/2007 |
| KR | 1020080065748 A | 7/2008 |

(Continued)

OTHER PUBLICATIONS

International Search Report and Written Opinion of the International Searching Authority issued Jul. 7, 2014 in connection with International Application PCT/US14/22606, 10 pages.

(Continued)

*Primary Examiner* — James Dudek

(57) ABSTRACT

A system is disclosed for repairing liquid crystal display panels that include a polarizing film. The system includes a laser repair optical system, a measurement optical system, and a processor. The laser repair optical system includes a polarization unit for modifying a polarization of a laser repair beam along a laser output path that is directed toward a workpiece. The measurement optical system includes an illumination source for providing measurement illumination along a measurement illumination path, and a detector for detecting reflected measurement illumination. The processor adjusts the polarization unit responsive to the reflected measurement illumination.

19 Claims, 11 Drawing Sheets

(56) References Cited

U.S. PATENT DOCUMENTS

| | | | |
|---|---|---|---|
| 2006/0065645 A1* | 3/2006 | Nakasu | B23K 26/34 219/121.68 |
| 2006/0087321 A1 | 4/2006 | Kawada et al. | |
| 2009/0141231 A1 | 6/2009 | Lim et al. | |
| 2010/0237051 A1* | 9/2010 | Gu | B23K 26/0003 219/121.68 |
| 2011/0062127 A1* | 3/2011 | Gu | B23K 26/04 219/121.69 |
| 2011/0210105 A1 | 9/2011 | Romashko et al. | |
| 2012/0103955 A1 | 5/2012 | Woo et al. | |

FOREIGN PATENT DOCUMENTS

| | | |
|---|---|---|
| KR | 1020100062283 A | 6/2010 |
| KR | 1020110137460 A | 12/2011 |

OTHER PUBLICATIONS

Written Opinion of PCT/US2014/022606, issued Sep. 15, 2015.

* cited by examiner

SYSTEMS AND METHODS FOR PROVIDING POLARIZATION COMPENSATED MULTI-SPECTRAL LASER REPAIR OF LIQUID CRYSTAL DISPLAY PANELS

BACKGROUND

The present invention relates generally to laser repair of electronic devices that include arrays of discrete circuits, any one of which may be isolated in the event that the discrete circuit is defective, and relates in particular to the repair of liquid crystal display panels.

Liquid crystal display (LCD) panels may generally include liquid crystal layer sandwiched between glass plate structures, one of which includes an array of transistor elements (having signal lines and gate lines) in a substantially transparent electrode layer. The other glass plate structure generally includes a large number of sets of color filters (e.g., red green and blue) forming color display pixels.

It is known that individual transistor elements may be defective upon manufacturing. The defects may cause the pixel to remain dark even when it is turned on, or may cause the pixel to remain bright when power is applied to the display panel but the pixel is turned off. It is further known that a dark pixel is not a considerable problem, as the human eye will likely not notice a tiny pixel in an overall panel failing to turn on. On the other hand, a bright pixel when it is intended to be dark is quite noticeable. Many procedures have been developed for attempting to reduce or eliminate the bright pixel defects.

U.S. Pat. Nos. 6,812,992; 7,502,094; and 7,755,380 for example, generally disclose using laser radiation to decrease the transmittance of the color filter of a damaged pixel. U.S. Pat. No. 5,142,386 discloses using laser radiation to disturb the orientation of the liquid crystal molecules, and to blacken the color filter of a damaged pixel. Other techniques involve cutting conductive portions of the transistor elements associated with the pixel to be repaired.

U.S. Pat. No. 7,636,148 discloses the use of a repair film (a transparent organic film) that is coated on the exposed outer surface of the device, wherein the repair film is specially designed to become opaque upon application of associated laser radiation. U.S. Pat. No. 7,697,108 disclose the darkening of damaged pixels by 1) forming a recess in the outer substrate aligned with the defective pixel, 2) depositing a UV curable resin in the recess, and 3) irradiating the resin with ultraviolet radiation.

The individual pixels (e.g., as defined by the color filters) do not contact one another, but are generally each surrounded by a black matrix material. U.S. Patent Application No. 2009/0141231 disclose darkening damaged pixels by applying laser radiation to portions of the black matrix to cause black matrix particles to become dispersed between the pigment layer and an upper substrate to thereby occlude the pixel. The reference also discloses using UV radiation to destroy the associated alignment layer to cause the liquid crystal molecules to become misaligned.

It is also known that applying laser radiation to films within a pixel may cause bubbles to be formed that may migrate to other regions of the liquid crystal panel compromising the functionality of neighboring pixels. U.S. Patent Application Publication No. 2006/0087321, for example, discloses using laser radiation to disrupt alignment films of damages pixels, and further that the repetition rate of the laser is controlled to provide that any bubble formed by the radiation is immediately targeted with another laser beam. The reference discloses that when the second laser energy hits the pixel that includes such a bubble, the laser illumination energy is mostly absorbed by alignment films, causing them to become evaporated. The evaporated components are disclosed to drift within the bubble and eventually settle as a dark film, decreasing the amount of light that passes through.

Many liquid crystal displays include a polarizing film or plate on at least the outer surface of the display device. The polarizing film or plate provides desired display viewing functionality, and may include a wide variety of polarization orientations at different portions of the film or plate. In devices that employ polarizing films or plates on an outer surface of the device, the pixel repair process is further complicated in that the varying polarization orientations will result in varying amounts of polarized laser energy being applied to defective pixels.

Although many procedures have been developed for darkening defective pixels in a liquid crystal display, there remains a need for such a system and method that overcomes drawbacks of conventional methods, such as for example, the difficulty in managing entrapped bubbles when the liquid crystal molecules are disturbed, and the difficulty in performing the processing steps when polarization films are employed in the liquid crystal display.

SUMMARY

In accordance with an embodiment, the invention provides a LCD repair system for repairing liquid crystal display panels that include a top polarizing film. The LCD repair system includes a laser repair optical system, a measurement optical system, and a processor. The laser repair optical system includes a polarization unit for modifying a polarization of a laser repair beam along a laser output path that is directed toward a workpiece. The measurement optical system includes an illumination source for providing measurement illumination along a measurement illumination path, and a detector for detecting reflected measurement illumination. The processor adjusts the polarization unit responsive to the reflected measurement illumination.

In accordance with another embodiment, the invention provides an LCD repair system for repairing liquid crystal display panels that include a polarizing film, wherein the LCD repair system includes a laser repair optical system, a processor, and a measurement optical system. The laser repair optical system includes a polarization unit for modifying a polarization of a laser repair beam along a laser output path that is directed toward a workpiece. The processor determines an optimal polarization of the laser repair beam to provide a desired laser energy at the workpiece. The measurement optical system includes an illumination source for providing measurement illumination along a measurement illumination path, and a detector for detecting reflected measurement illumination. The processor determines an adjustment for adjusting the polarization unit responsive to the optimal polarization of the laser repair beam to provide a desired laser energy at the workpiece and the reflected measurement illumination.

In accordance with a further embodiment, the invention provides a method of repairing an LCD display. The method includes the steps of: providing a laser repair optical system that includes a polarization unit for modifying a polarization of a laser repair beam along a laser output path that is directed toward a workpiece; determining an optimal polarization of the laser repair beam to provide a desired laser energy at the workpiece; providing a measurement optical system that includes an illumination source for providing measurement illumination along a measurement illumination path; detecting reflected measurement illumination; and determining an adjustment for adjusting the polarization unit responsive to the optimal polarization to provide a desired energy at the workpiece, and the reflected measurement illumination.

BRIEF DESCRIPTION OF THE DRAWINGS

The following description may be further understood with reference to the accompanying drawings in which.

The drawings are shown for illustrative purposed only.

DETAILED DESCRIPTION

A liquid crystal Display (LCD) is a sandwich of different functional layers generally including a top polarizer, a color filter array, a liquid crystal, a bottom polarizer and an illuminator. Each of the polarizers has a polarization axis corresponding to the polarization axis of light that is transmitted through the respective polarizer. The liquid crystal is controlled to rotate the polarization axis of light between the top and bottom polarizers and thereby control transmission of light though the LCD.

Figure 1:
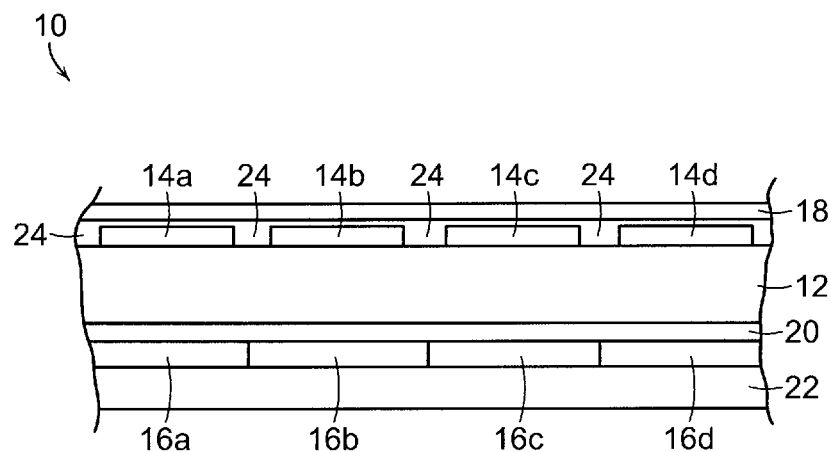
FIG. 1 shows an illustrative diagrammatic partial cross-sectional view of a liquid crystal display in which a repair system and process may be employed in accordance with an embodiment of the present invention.

As shown in FIG. 1, an LCD may include a liquid crystal layer 12, a plurality of color filters 14a, 14b, 14c and 14d, a transparent electrode layer including individual transistor elements 16a, 16b, 16c and 16d a top polarizing film 18, a lower polarizing film 20 and an illumination panel 22. The color filters may be provided in sets of three, for example, where color filters 14a and 14d are red, color filter 14b is green and color filter 14c is blue. As further shown in FIG. 2, the array of color filters may be provided within a matrix 24 of a black plastic material to minimize transmission of undesired light. As used herein, the term pixel may refer to a picture element associated with one or more transistor elements of the electrode layer and/or one or more color filters where the display is a color display.

Figure 2:
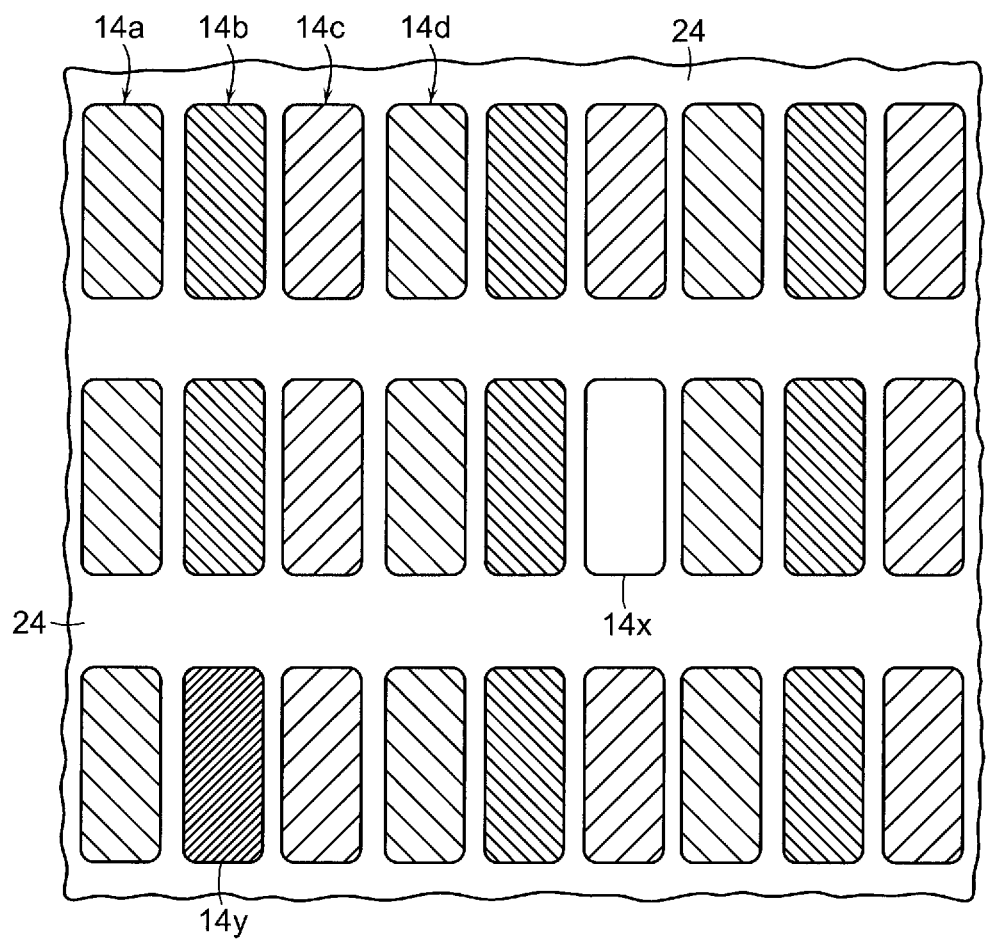
FIG. 2 shows an illustrative diagrammatic plan view of a liquid crystal display panel that show three color filters, one pixel that is defectively remains dark and one pixel that defectively remains lighted.

As also shown in FIG. 2, the display may include pixels having defects. For example, the pixel associated with color filter 14x is shown as emitting undesired light (a bright pixel defect), and the pixel associated with color filter 14y is shown as not emitting desired light (a dark pixel defect).

The bright pixel defects are to be repaired, for example by darkening the pixels exhibiting the bright pixel defects. Repair may entail irradiating a portion of the LCD to change material properties to reduce the amount of illumination through a bright pixel defect area. As discussed above, various laser based repair techniques are known, for example cutting conductive elements to repair or disable pixel function and darkening of color filter material directly or indirectly by laser irradiation.

Figure 3A:
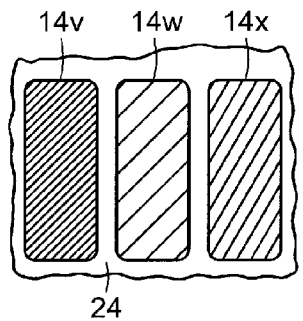
FIGS. 3A-3C show illustrative diagrammatic plan views of a portion of a liquid crystal display panel at three points in time during which a laser repair beam is employed to darken a selected pixel.
Figure 3B:
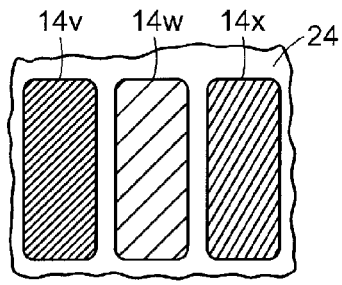
Figure 3C:
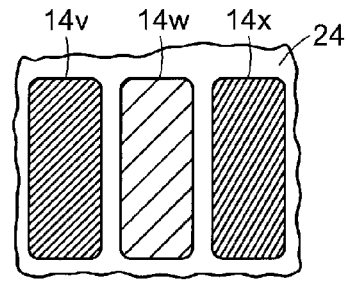
Figure 3D:
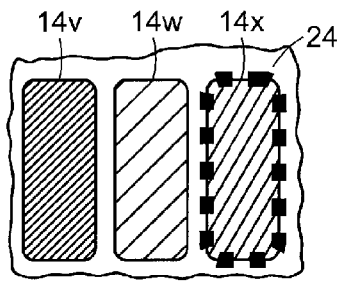
FIGS. 3D and 3E shows illustrative diagrammatic views of a portion of the liquid crystal display panel when portions of the black matrix is employed to darken a selected color filter.
Figure 3E:
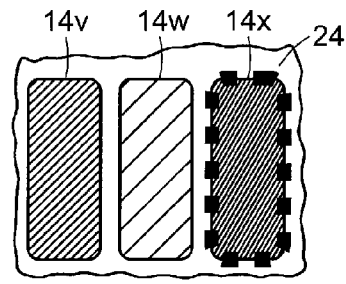

As shown, for example, in FIGS. 3A-3C, the color filter 14x associated with a bright pixel defect may be darkened by applying laser radiation directly to color filter 14x in a predetermined scan pattern. In another embodiment, the color filter may be darkened by applying laser radiation to modify the black matrix material 24 that surrounds the color filter 14x as shown in FIG. 4D, and then (using the scanned laser) dispersing the disturbed black matrx material over the color filter as shown in FIG. 3E. Alternatives to laser repair procedures may include mechanical operations such as inking bright defects.

Figure 4:
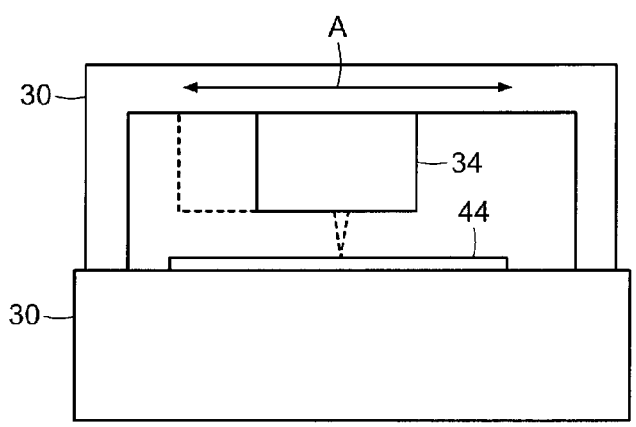
FIG. 4 shows an illustrative diagrammatic schematic view of a gantry system in accordance with an embodiment of the invention.

As shown in FIG. 4, a gantry 30 carries the optical repair head 34 over the workpiece (LCD 44), in part, as shown at A, and positions the repair head over defective pixels that need to be repaired. Other well-known relative position systems such as stacked and split stages may alternately be used to position the optical repair head over defective pixels. Relative motion may be in the range of a few hundred millimeters to greater than 1 meter. It is expected that the range of relative motion will continue to increase to accommodate larger panels and available mother glass substrates sizes. For example current mother glass sizes range from $1^{st}$ generation 300 mm×400 mm to 10$^{th}$ generation 2850 mm×3050 mm. The function of the optical head is largely independent of the range of motion over the LCD panel, although large substrates with many repairs benefit from fast repair and increased throughput.

Figure 5:
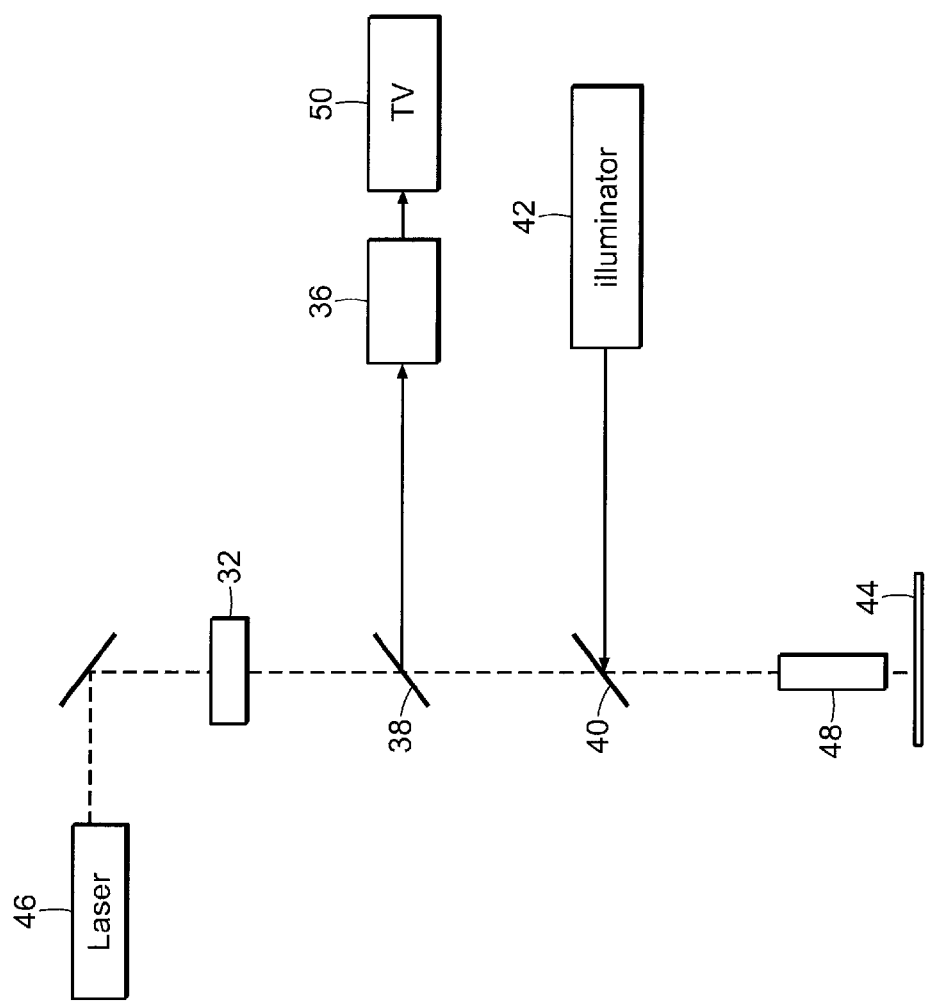
FIG. 5 shows an illustrative diagrammatic schematic view of an optical repair head in accordance with an embodiment of the invention.

As shown in FIG. 5, the laser repair optical system includes a laser system 46, a rotary half wave plate 32, beam splitters 38, 40, and an objective 48. The measurement optical system includes an illuminator 42, the beam splitters 38, 40, the objective 48, a detector 36 and a video device 50. The optical paths are coincident between beam splitter 38 and the workpiece, and both optical paths are directed toward the workpiece support structure that carries the LCD panel 44 that is to be repaired using the output of a laser system 46. The illuminator 42 provides illumination that is reflected from a portion of the workpiece, and from the reflection, the detector 36 determines the polarization of that portion of the polarization layer on the workpiece. The optical subsystem includes at least one high magnification imaging system 50 for viewing pixel structures.

The laser subsystem includes a laser system for processing defective elements by irradiating the LCD. The imaging system field of view includes at least a portion of the color filter array and some non-filter area. Preferably, the imaging system comprises a color corrected imaging objective such as a microscope objective to provide images to an image sensor such as a video camera and outputs image signals, raw image files to be processed or processed image files. The imaging system may also include image processing capability such as pattern matching or pixel averaging, and may output processed images or calculated image values. The imaging system may further include other well-known imaging elements such as relay lenses or tube lenses to provide a focused image to the camera having a predetermined magnification and resolution. Preferably, the imaging system also includes a coaxial illuminator to illuminate the field of view from the top side. Other types of illumination may be used such as off-axis top side illumination or illumination transmitting up from the bottom side of the LCD.

The laser system 46 includes one or more laser sources generating suitable repair beams. Generally, in a multispectral embodiment, multiple wavelengths are used to perform different repair tasks such as darkening different color sub-pixels in the array. For example, a green laser output (e.g., 515 nm) may be used to irradiate red color filters and/or cut electrical data lines, and a red laser output (e.g., 1030 nm) may be used to irradiate green and blue color filters. In some embodiments, a UV output (e.g., 343 nm) may be employed in certain applications. For convenience, the laser output is referred to as the repair beam, but it will be understood that this may be a single wavelength laser beam, multiple laser beams at multiple wavelengths and laser beams with varying powers and pulse properties, for example infrared, ultraviolet, and ultrashort pulse lasers, as long as the laser output transmits though an objective lens to irradiate the LCD. The laser output may be generated by a single laser controlled to vary the output properties or multiple lasers with different output properties combined into the repair beam.

Figure 6:
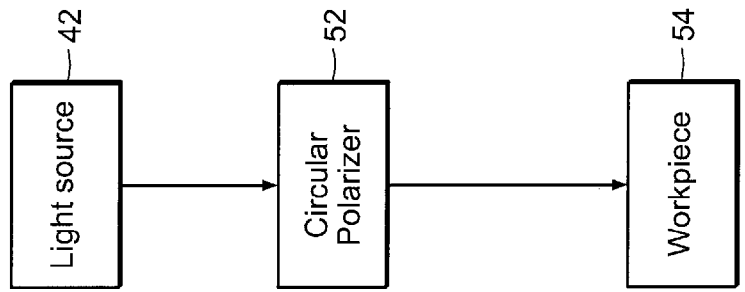
FIG. 6 shows an illustrative diagrammatic schematic view of a system in accordance with an embodiment of the present invention which a fixed polarizer is employed.

The laser repair beam is directed to impinge the workpiece within the field of view of the imaging system. Preferably, to direct the repair beam to the workpiece, the repair beam is controllably deflected to provide random access on the workpiece within a deflection field. Different types of optical deflectors may be used for, for example in at least one embodiment as shown in FIG. 6 the deflector is a 2-axis acousto-optic beam deflector (AOBD) including an X-axis AOBD deflector 56 and a Y-axis AOBD deflector 58. Various aspects of beam deflection are described in U.S. Patent Application Publication No. 2011/0210105, the disclosure of which is hereby incorporated by reference in its entirety. The AOBD provides fast beam positioning and laser pulse energy control; in some cases deflection is on a pulse by pulse basis.

The laser repair beam then passes through relay optics 60 prior to reaching the LCD display 44. Deflection scan patterns 62 within the deflection field may irradiate the area of one or more sub-pixels in a single pass or in multiple passes. A specific pattern may be associated to the particular material irradiated and may be for example a raster, a dither or a diffusion pattern. The irradiation regimen includes controlled laser output properties and a deflection pattern that may be determined for example from identifying a defect in an acquired image.

Combinations of laser parameters and deflection patterns may be electronically stored and retrieved for use based on an acquired image. Other types of deflectors may be used including galvanometer scanners, fast steering mirrors and the like. These mirror based deflectors have the advantage that deflection angle is independent of wavelength as well as larger scan angles, however acousto-optic deflectors provide faster random access within the scan field and energy control without an additional modulator. In further applications, other types of deflectors may include electro-optic deflectors.

When a multispectral output is employed that includes for example, 447 nm (for frequency tripled 1343 (blue)) and 671 nm wavelengths, each wavelength may be deflected with different sets of optical scanners or may be commonly deflected with a single multiple axis deflector set that is designed to work at the multiple laser wavelengths. Each deflector in the set may be an AOBD having different center frequencies for each wavelength such that the center deflection angle for each wavelength is within a predefined tolerance such as 4 mrad or less with an optimized diffraction efficiency of at least 70% and a diffraction angle scan of about 37 mrad. An advantage of AOBDs is that full very fine energy control of the beam energy (same as AOM) may be obtained, as well as the deflection. Further, fine energy control is crucial to being able to set up a very low level, non destructive measurement beam and to set the processing energy. Suitable TeO$_2$ devices are available for example from Gooch & Housego PLC of Somerset, United Kingdom (formerly Crystal Technologies, LLC).

The laser system includes at least one optical element to modify the polarization state of the repair beam. Polarization is modified to increase coupling to the workpiece through the top polarizer. In some cases, depending on the relative orientation of a linearly polarized repair beam and the top polarizer, a circular polarizer modifies the repair beam to increase coupling.

As shown in FIG. 6 for example, in an embodiment, the light source 42 may provide illumination to a circular polarizer 52 prior to reaching the workpiece 54. Since in this case the modified polarization is circular by design, the modified beam is thereby desensitized to the orientation of the LCD top polarizer and the circular polarization should transmit uniform energy to the color filter regardless of orientation errors in the top polarizer axis.

In practice, the beam may not be perfectly polarized and the circular polarization may be impure (e.g., elliptical) resulting in energy coupling that varies with orientation of the top polarizer. For example, coupling may vary by as much as 10% even with a circular polarizer in the beam path. Further, circular polarization may not fully optimize coupling of energy to LCD structure lying below the top polarizer. Even if circular polarization is ideal and energy transmission is uniform with varying orientations of the top polarizer, roughly half of the energy will be absorbed in the top polarizer reducing processing energy at the underlying structure to be processed. Moreover, energy absorbed in the top polarizer may cause damage. Both of these effects can limit the processing energy window to undesirable levels.

Figure 8:
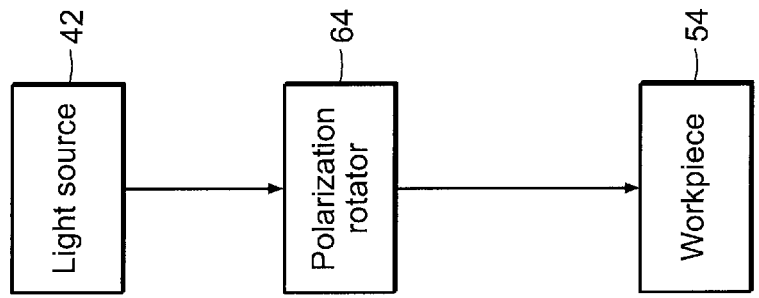
FIG. 8 shows an illustrative diagrammatic schematic view of a system in accordance with an embodiment of the present invention which a variable polarizer is employed.
Figure 7:
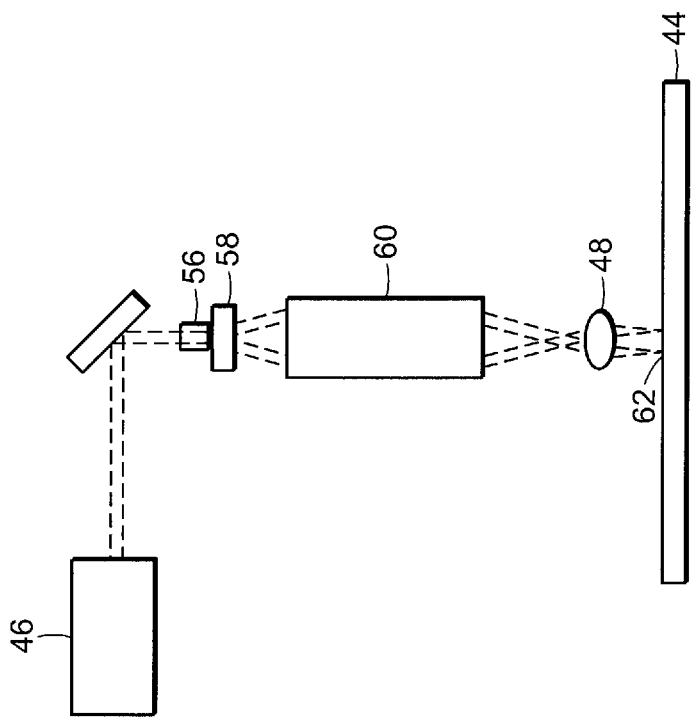
FIG. 7 shows an illustrative diagrammatic schematic view of an optical assembly of a system in accordance with an embodiment of the present invention.

Energy coupling can be increased when a linearly polarized repair beam is aligned to the top polarizer by rotation as shown in FIG. 8 where laser output from light source 42 is adjusted by a polarization rotator 64 prior to reaching the workpiece 54. When the alignment of the top polarizer axis is sufficiently accurate, processing beam linear polarization may be aligned accordingly for processing. Polarization rotation can be accomplished with a halfwave plate that is rotatable in the laser path. For a multispectral system, each laser beam may be independently rotated with a wavelength specific halfwave plate, or different beams sharing an optical path can be rotated using an achromatic waveplate. In either case, zero-order waveplates are preferred over multiple order waveplates. Alternately using other known polarization rotation techniques, linear polarization may be modified to be aligned with the top polarizer axis.

It is known that linear polarization may be rotated at twice the angle of the half-wave plate. Thus, 360 degrees of polarization rotation can be achieved with 180 degrees of mechanical rotation. In some cases, the polarization range may be 180 degrees with 90 degrees of mechanical rotation. Skilled practitioners will recognize that alternative polarization rotators may be used such as image rotators, Pockels cells and the like. Various types of known control electronics may be used to drive actuators and mechanically rotate polarization or to drive other types of optical or electro-optical polarization rotators for solid state polarization rotation.

The orientation of the polarization axis of the top polarizer is poorly controlled and the axis orientation may even vary across the workpiece. Resulting orientation errors may be several 10's of degrees. Static alignment or alignment to a predetermined nominal orientation therefore, may result in substantial orientation errors and as a consequence energy coupling errors that limit the efficacy of laser repair processes. In view of these limitations in nominal linear polarizer orientation, it is recognized that a linearly polarized repair beam aligned to the actual polarization axis of the top polarizer can improve coupling at one or more repair sites.

In order to locally optimize polarization alignment, measurement of the top filter polarization axis is used as a reference to minimize polarization alignment errors and maximize energy coupling for more effective repair procedures. Furthermore, rapid measurement is preferred to provide high throughput. In at least one embodiment as shown in FIG. 9, the optical repair head includes a detector 66 for detecting illumination reflected off of the workpiece 54 (of FIG. 8) and adjustment of the polarization rotator 64 is automatically controlled.

Figure 10:
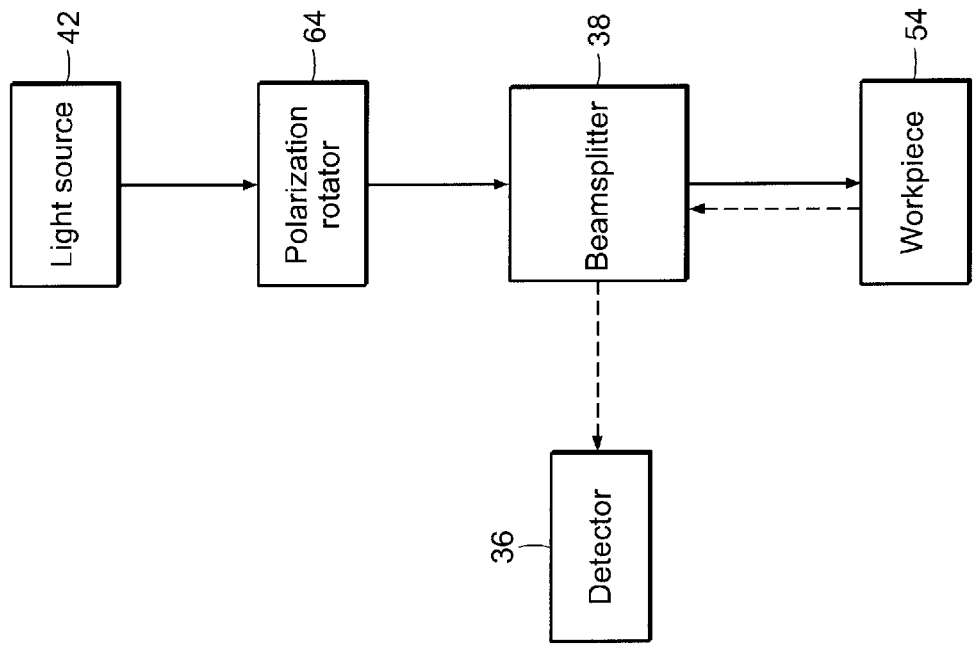
FIG. 10 shows an illustrative diagrammatic schematic view of a system of a further embodiment of the present invention in which a detector is employed in a coaxial embodiment.
Figure 9:
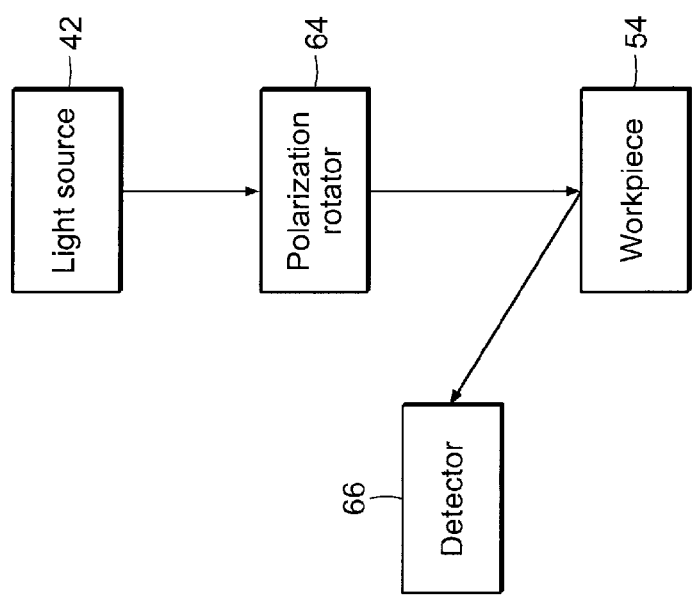
FIG. 9 shows an illustrative diagrammatic schematic view of a system of the invention in which a detector is employed in a non-coaxial embodiment.

Again, with reference to FIG. 9, reflected light may propagates to the detector coaxial with the incident laser processing beam axis, and the returning reflection path is then separated for example with a beamsplitter 38 and be directed to a detector 36. In another example depicted schematically in FIG. 10, the detector 36 receives non-coaxial reflected light at an angle to the axis of the processing beam. Such an arrangement may be used to eliminate one or more beam splitters from the optical path of the laser processing beam axis. Maximizing the reflection off of the LCD corresponds to alignment of the repair beam polarization axis and the top filter polarizations axis. This is believed to be due primarily to minimized absorption in the top filter.

Figure 11:
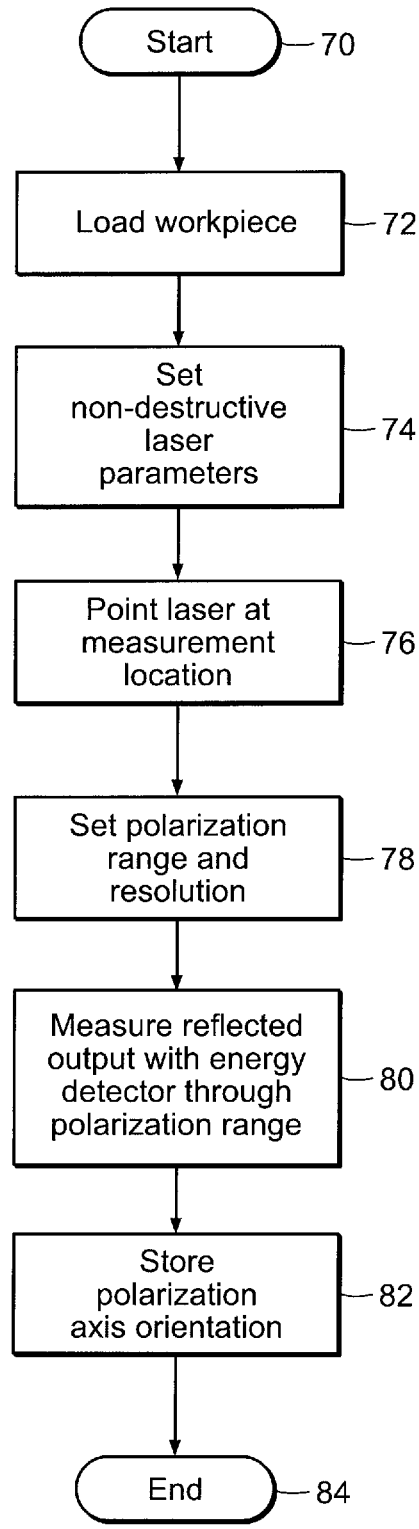
FIG. 11 shows an illustrative diagrammatic flow diagram of a polarization axis measurement process in accordance with an embodiment of the invention.

With reference to FIG. 11, a polarization measurement process begins (step 70) with having the workpiece loaded (step 72) and the measurement laser source is set to be non-destructive (step 74). The beam is directed to a measurement location on the workpiece (step 76), the polarization orientation of the measurement beam is set in a range of orientations (step 78), and the reflection from the workpiece is measured through the range of relative orientations (step 80). The maximum reflection is determined from the acquired data and this orientation set (step 82) and used for subsequent repair procedures at or near the measurement location. The measurement process then ends (step 84). The measurement source may be a laser repair beam source set to be non-destructive, but the measurement source could be an additional dedicated light source.

Figure 12:
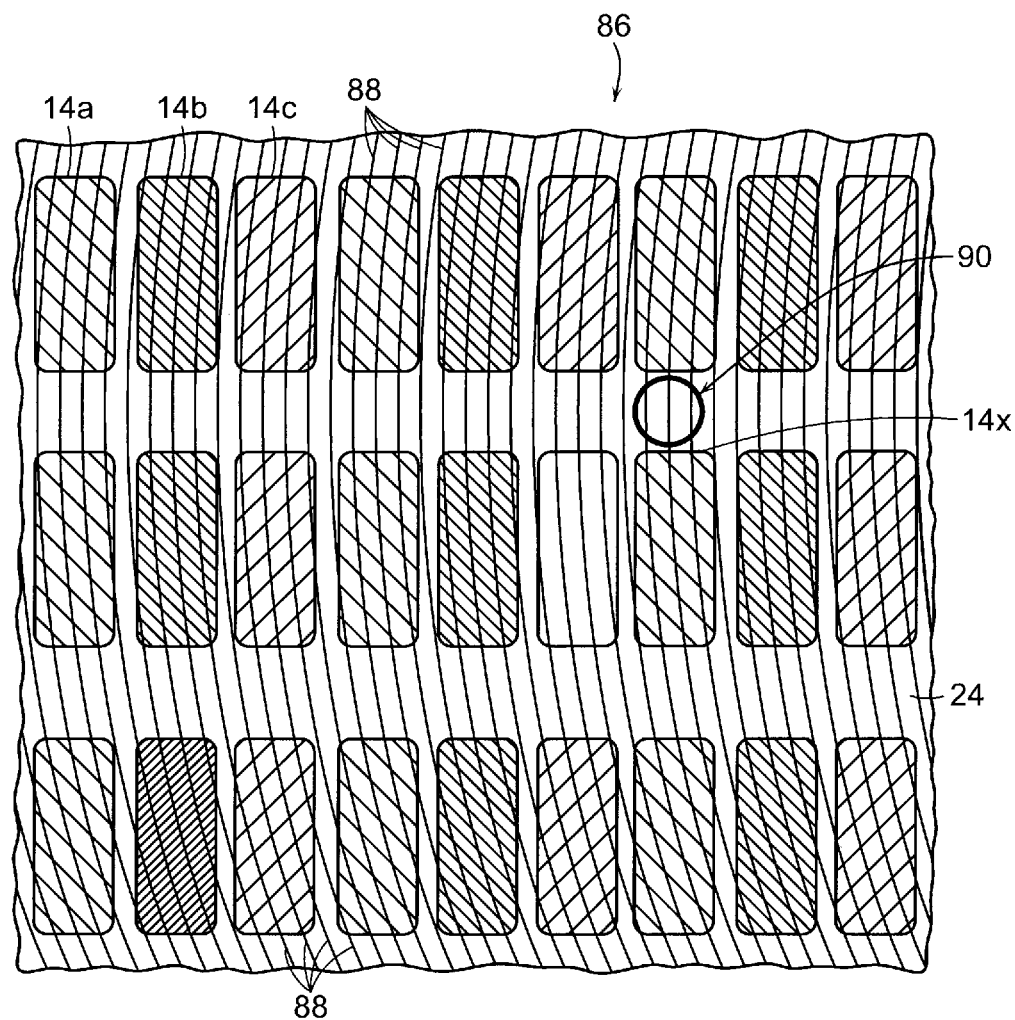
FIG. 12 shows an illustrative diagrammatic plan view a liquid crystal display for repair in accordance with an embodiment of the present invention that includes a polarization layer.

Within the field of view of the beam deflector, different materials lay under the top polarizer as shown at 86 in FIG. 12. In addition to the color filers discussed above with reference to FIG. 2, FIG. 12 also shows diagrammatically the polarization film having lines of polarization 88 For measurement of the polarization axis, a relatively high reflectance material may be selected as in a region of interest as a reflector for measurement. In other words, the area 90 may be one of many reflector regions distributed over the device. As shown at 90, an area of the black matrix 24 is chosen for polarization measurement.

Figure 13:
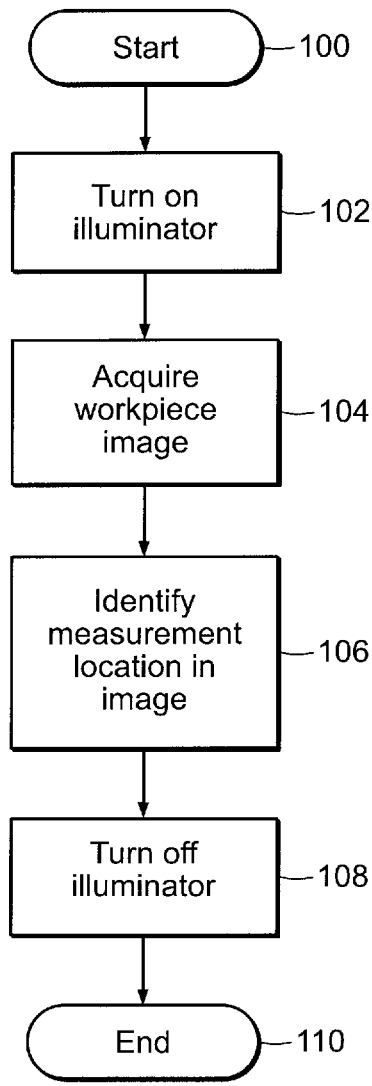
FIG. 13 shows an illustrative diagrammatic flow diagram of a process for identifying a measurement location in accordance with an embodiment of the invention.

With reference to FIG. 13, the process begins (step 110) by having the illumination turned on (step 102), an image of the LCD is acquired (step 104), and the location of the preferred material for measurement identified within the field of view of the deflector (step 106). The location may be determined, for example using image processing techniques or may be performed manually or semi-automatically by an operator. After identifying the measurement location, the illumination is turned off (step 108) for subsequent measurements and the process ends (step 110).

Figure 14:
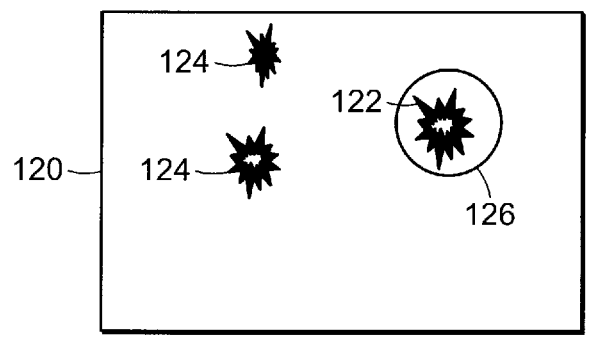
FIG. 14 shows an illustrative diagrammatic plan view of a measurement reflection in accordance with a measurement process of the present invention.
Figures 15, 16:
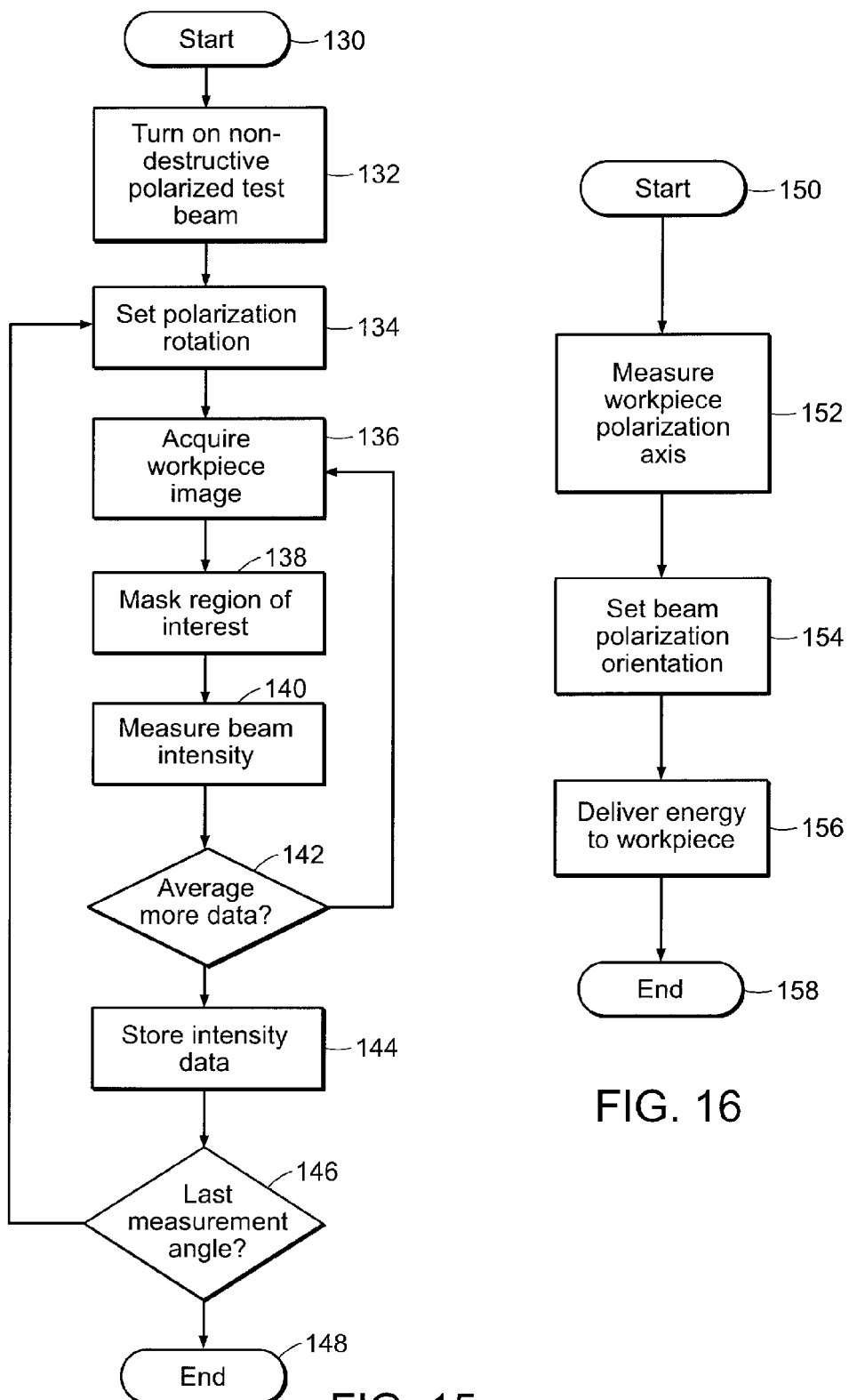
FIG. 15 shows an illustrative diagrammatic flow diagram of a measurement process in accordance with an embodiment of the invention.
FIG. 16 shows an illustrative diagrammatic flow diagram of a repair process in accordance with a non-calibrated energy embodiment.

As shown diagrammatically in FIG. 14, irradiation of the measurement area 120 may result in undesired reflections 124 that degrade measurement accuracy of the desired reflection 122. A mask may 126 therefore be employed to isolate the region of interest. With reference to FIG. 15, this measurement process begins (step 130) by turning on the non-destructive polarized test beam (step 132), setting a polarization rotation (step 134), acquiring an image (step 136), and masking a region of interest (step 138). The step of masking an area of interest may involve surrounding the measurement location based on a desired measurement reflection and unwanted reflections to be excluded. For example, pixel intensity may be integrated only over an area of interest rather than the entire image frame and multiple measurements may be taken for sample averaging to improve measurement accuracy. In particular, after the beam intensity is measured (step 140), the process determines whether more data should be averaged (step 142), and if so, the process returns to step 136 as shown.

This type of spatial filtering is performed during image processing where extraneous reflections are automatically masked. When no more data is determined to be needed for averaging (step 142), the process stores the intensity data (step 144) and returns to step 134 unless the measurement angle is the last measurement angle to be measured (step 146), in which case the process ends (step 148). The laser output energy and/or detector gain may be adjusted prior to detection to ensure that the detector is not saturated, and generally background illumination will be minimized for accurate measurements. For example, a field illuminator could be turned off prior to measurement.

The detector may be a camera, but other types of detectors sensitive to reflected laser radiation reflected off of the workpiece may also be used in place or in addition to a camera, for example additional detectors may improve measurement sensitivity to the reflected light. The detector camera may also be used for aligning the workpiece or a second dedicated camera may be used for improved throughput and or measurement accuracy.

With reference to FIG. 16, in a non-calibrated energy embodiment the process begins (step 150) by measuring a workpiece polarization axis (step 152). The beam polarization orientation is then set (step 154), and energy is delivered to the workpiece (step 156). The orientation of the top polarizer is determined/measured based on the reflections, and the repair beam is then adjusted to align with top polarizer. The repair beam is then delivered to the workpiece (step 156) and the process ends (step 158). Polarization measurement and alignment may be performed at each repair site to overcome variability of the top filter polarization axis and provide optimized energy coupling at each repair site.

Figure 17:
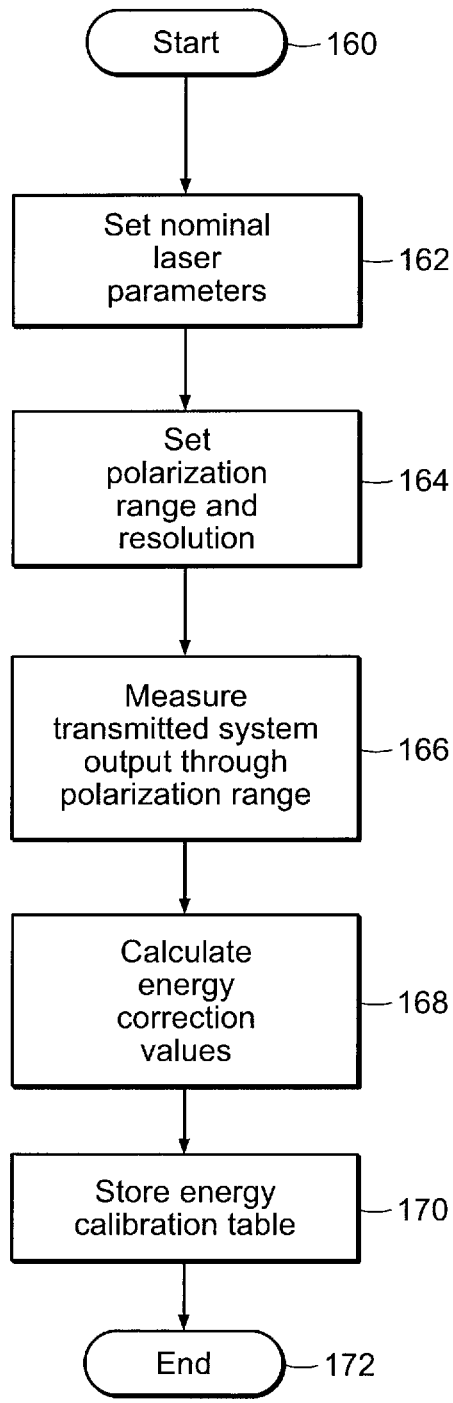
FIG. 17 shows an illustrative diagrammatic output energy versus polarization calibration process in accordance with an embodiment.

When polarization of the measurement is rotated, energy of the output directed to the workpiece surface should be stable, for example, equipment should be warned up and thermally settled. Output however, may vary due to polarization sensitivity of beam path elements such as beamsplitters and folding mirrors. This output error will result in measurement error and repair energy setting errors when polarization is rotated. With reference to FIG. 17 a calibration routine may consider both output energy and polarization. The process begins (step 160) by having nominal laser parameters set (step 162), and polarization range and resolution are set (step 164). Laser output is then measured through the range of polarization rotations and variations are measured (step 166), and energy correction values are calculated (step 168) to generate an output calibration table (step 170). The process then ends (step 172). Laser output may be measured at the workpiece surface using a power or energy meter. The detector may be located contiguous with the substrate at or near the plane of the workpiece as disclosed, for example, in U.S. Pat. No. 6,501,061, the disclosure of which is hereby incorporated by reference in its entirety.

Figure 18:
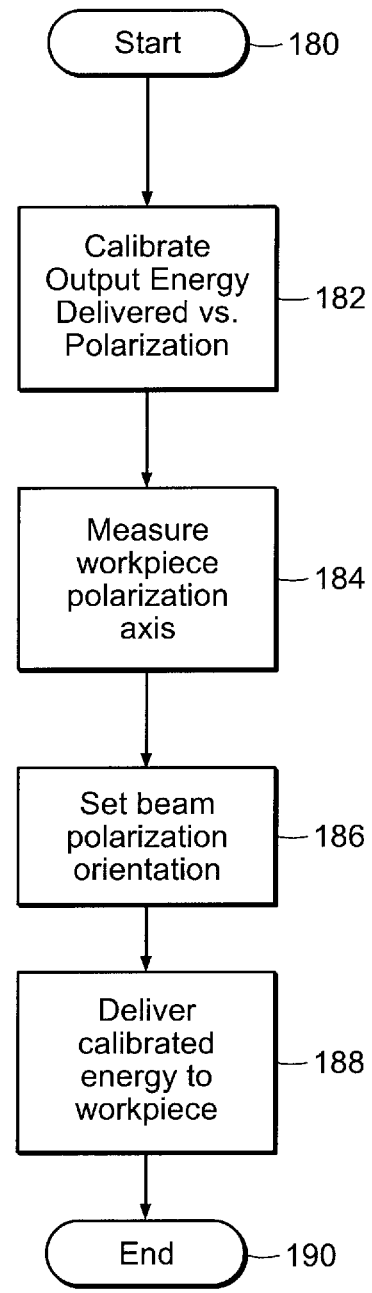
FIG. 18 shows an illustrative diagrammatic repair process in a calibrated energy embodiment.

With reference to FIG. 18, the calibrated energy values may be employed in a compensated repair process that begins (step 180) by calibrating output energy delivered versus polarization (step 182) as discussed above with reference to FIG. 16. The workpiece polarization axis is then measured (step 184), the beam polarization is then set (step 186) and the calibrated energy is then delivered to the workpiece (step 188). The process then ends (step 190). The calibration is therefore applied to the measurement beam to provide calibrated energy for polarization axis measurement. The polarization orientation is set accordingly for the repair procedure and calibrated energy is delivered to the workpiece. In this way transmission is maximized, because it's important that not too much energy be absorbed into the polarizer. Also, consistent (and correct) energy is transmitted and delivered to the color filter for laser repair because the process window is typically narrow and the actual optimum energy to darken the color filter is determined very carefully to avoid unintended damage to the LCD. For calibration and measurement steps, preferably the laser will be stabilized for a predetermined time.

Figure 19:
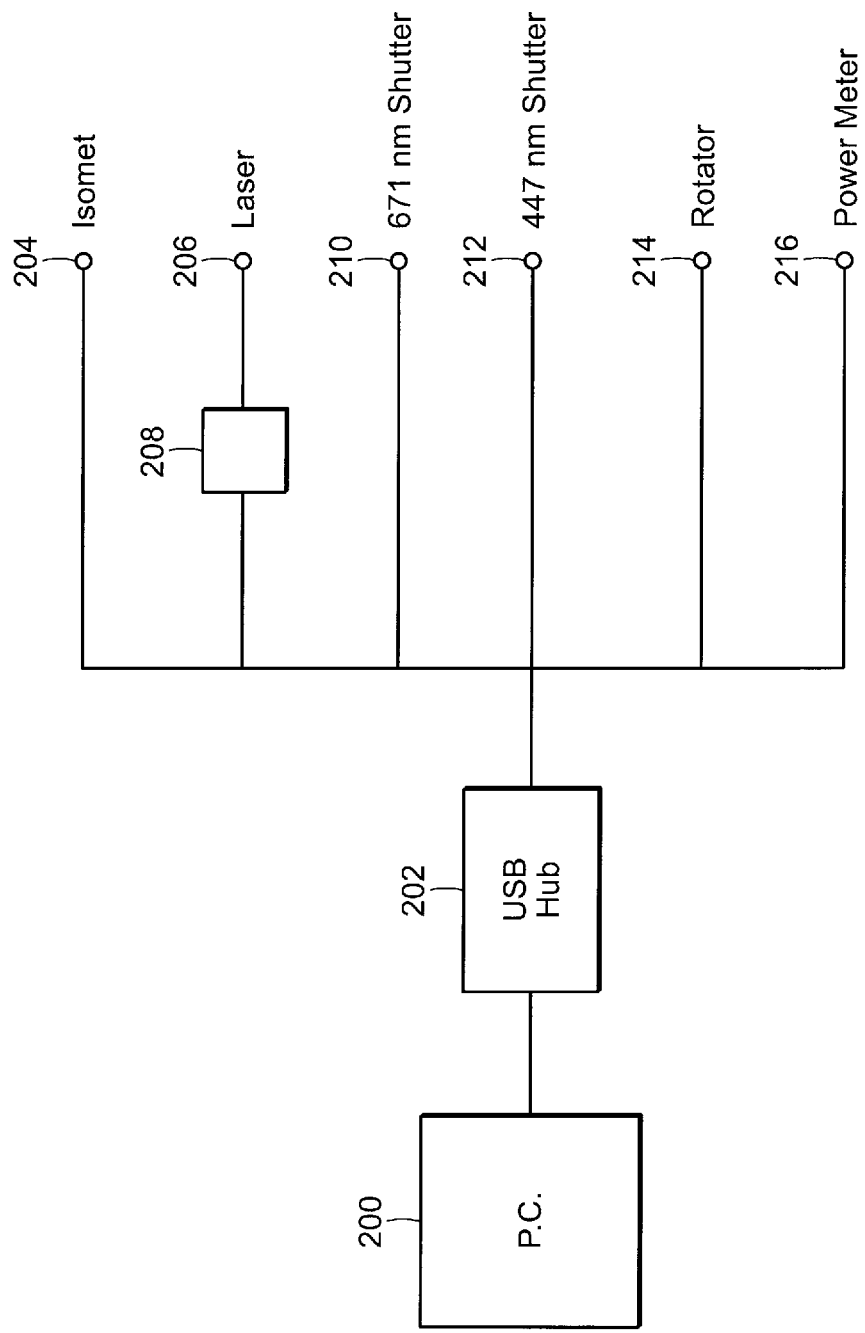
FIG. 19 shows an illustrative diagrammatic schematic view of a control system for a system in accordance with an embodiment of the invention.

As shown in FIG. 19, the control system may include a computer such as personal computer 200 that is coupled to a USB powered hub 202, which in turn is coupled to an Isomet iHHS controller 204, the laser system 206 (via an RS232 converter), a shutter for a 671 nm repair beam 208, a shutter for a 447 nm repair beam 210, the polarization rotator 214, and a power meter 216 such as a Coherent Powermax UV/VIS power meter as sold by Coherent, Inc. of Santa Clara, Calif.

Those skilled in the are will appreciate that numerous modification and variations may be made to the above disclosed embodiments without departing from the spirit and scope of the present invention.

What is claimed is:

1. An LCD repair system for repairing liquid crystal display panels that include a polarizing film, said system comprising:
    a laser repair optical system that includes a polarization unit for modifying a polarization of a laser repair beam along a laser output path that is directed toward a workpiece;
    a measurement optical system that includes an illumination source for providing measurement illumination along a measurement illumination path, and a detector for detecting reflected measurement illumination; and
    a processor for determining an adjustment for the polarization unit responsive to the reflected measurement illumination.

2. The LCD repair system as claimed in claim 1, wherein said system further includes a laser source for providing laser outputs at a plurality of wavelengths.

3. The LCD repair system as claimed in claim 1, wherein said laser output path and said measurement illumination path are coaxial for at least a portions of said laser output path and said measurement illumination path.

4. The LCD repair system as claimed in claim 1, wherein said polarization adjustment unit is a rotatable ½ half wave plate.

5. The LCD repair system as claimed in claim 1, wherein said laser output path includes an X-axis AOBD and a Y-axis AOBD.

6. The LCD repair system as claimed in claim 1, wherein said processor includes an energy calibration table having energy correction values for different polarizations.

7. The LCD repair system as claimed in claim 1, wherein said system includes calibration means for determining an optimal polarization of the laser repair beam to provide a desired laser energy at the workpiece.

8. An LCD repair system for repairing liquid crystal display panels that include a polarizing film, said system comprising:
    a laser repair optical system that includes a polarization unit for modifying a polarization of a laser repair beam along a laser output path that is directed toward a workpiece;
    a processor for determining an optimal polarization of the laser repair beam to provide a desired laser energy at the workpiece;
    a measurement optical system that includes an illumination source for providing measurement illumination along a measurement illumination path, and a detector for detecting reflected measurement illumination; and
    wherein the processor determines an adjustment for adjusting the polarization unit responsive to the optimal polarization to provide a desired energy at the workpiece, and the reflected measurement illumination.

9. The LCD repair system as claimed in claim 8, wherein said system further includes a laser source for providing laser outputs at a plurality of wavelengths.

10. The LCD repair system as claimed in claim 8, wherein said laser output path and said measurement illumination path are coaxial for at least a portions of said laser output path and said measurement illumination path.

11. The LCD repair system as claimed in claim 8, wherein said polarization adjustment unit is a rotatable ½ half wave plate.

12. The LCD repair system as claimed in claim 8, wherein said laser output path includes an X-axis AOBD and a Y-axis AOBD.

13. The LCD repair system as claimed in claim 8, wherein said processor includes an energy calibration table having energy correction values for different polarizations.

14. A method of repairing an LCD display, said method comprising the steps of:
   providing a laser repair optical system that includes a polarization unit for modifying a polarization of a laser repair beam along a laser output path that is directed toward a workpiece;
   determining an optimal polarization of the laser repair beam to provide a desired laser energy at the workpiece;
   providing a measurement optical system that includes an illumination source for providing measurement illumination along a measurement illumination path;
   detecting reflected measurement illumination; and
   determining an adjustment for adjusting the polarization unit responsive to the optimal polarization to provide a desired energy at the workpiece, and the reflected measurement illumination.

15. The method of repairing an LCD display as claimed in claim 14, wherein said method further includes the step of providing laser outputs at a plurality of wavelengths.

16. The method of repairing an LCD display as claimed in claim 14, wherein said laser output path and said measurement illumination path are coaxial for at least a portions of said laser output path and said measurement illumination path.

17. The method of repairing an LCD display as claimed in claim 14, wherein said polarization adjustment unit is a rotatable ½ half wave plate.

18. The method of repairing an LCD display as claimed in claim 14, wherein said laser output path includes an X-axis AOBD and a Y-axis AOBD.

19. The method of repairing an LCD display as claimed in claim 14, wherein said step of determining an adjustment for adjusting the polarization unit responsive to the optimal polarization to provide a desired energy at the workpiece, and the reflected measurement illumination involves accessing an energy calibration table having energy correction values for different polarizations.

* * * * *